United States Patent [19]

Kutney

[11] 4,279,817
[45] Jul. 21, 1981

[54] METHOD FOR PRODUCING DIMER ALKALOIDS

[75] Inventor: James P. Kutney, Vancouver, Canada

[73] Assignee: The United States of America as represented by the Department of Health & Human Services, Washington, D.C.

[21] Appl. No.: 582,373

[22] Filed: May 30, 1975

[51] Int. Cl.$^3$ .................................................. C07D 519/04
[52] U.S. Cl. .................................. 260/244.4; 424/262
[58] Field of Search ........................................ 260/244.4

[56] References Cited

U.S. PATENT DOCUMENTS 4,199,505  4/1980  Szántay et al. ................... 260/244.4

OTHER PUBLICATIONS

Treasurywala et al., Dissertation Abstracts, p. 2666B, Dec. 1974.

Primary Examiner—Donald G. Daus
Assistant Examiner—D. Rivers
Attorney, Agent, or Firm—John S. Roberts, Jr.

[57] ABSTRACT

A concerted process for the synthesis of a dimer consisting of an indole unit and a dihydroindole unit possessing natural stereochemistry which comprises:
- (a) forming an N-oxide intermediate from said indole unit;
- (b) treating said N-oxide indole intermediate in the presence of acetic anhydride or halogenated derivative thereof to effect a Polonovski-type fragmentation reaction;
- (c) without isolating the N-oxide indole intermediate and at a temperature of about $-10°$ C. to $+10°$ C., coupling said reaction product with a dihydroindole unit in the presence of acetic anhydride or a halogenated derivative thereof at a low temperature of about $-10°$ C. to $+10°$ C. under inert conditions; and
- (d) subsequently reducing the immonium nitrogen on the indole unit by reacting with aqueous alkali metal borohydride to produce a dimer.

5 Claims, No Drawings

METHOD FOR PRODUCING DIMER ALKALOIDS

The present invention relates to an improved method particularly for producing dimer alkaloid compounds especially of the Vinca alkaloid group and in particularly is an improved method for producing the antiviral, antileukemic compounds vincristine and vinblastine of the following formula:

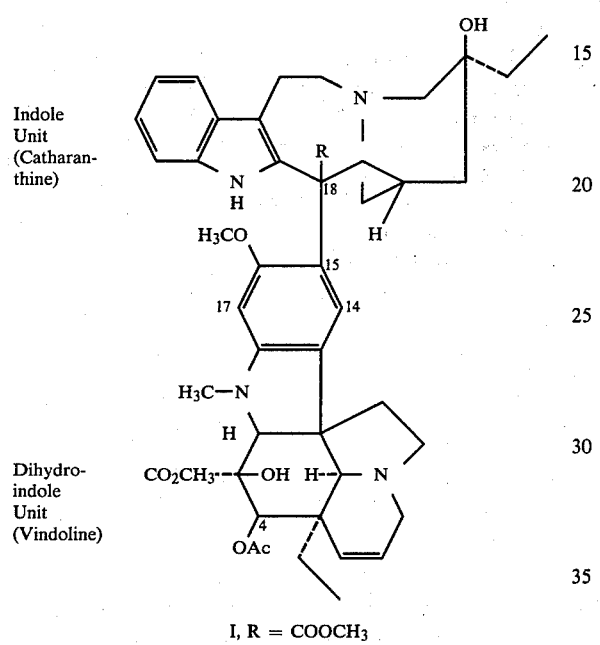

I, R = COOCH$_3$

The above compound is vinblastine (NSC 49482) and when $N_1{}^- = N\text{---}CHO$ (N-formyl) it is vincristine (NSC 67574).

The present series of dimeric alkaloids, including important antitumor agents, are formed from an indole, such as catharanthine, and a dihydroindole unit, e.g., vindoline, in which the halves are linked via a carbon-carbon bond involving an aliphatic center $C_{18}$ in the indole unit and an aromatic carbon $C_{15}$ in the vindoline portion. Specifically, where the catharanthine unit possesses a hydroxyl group at $C_4$, the dimer produced with vindoline will be vinblastine and also the similar catharanthine unit linked to formyl vindoline will produce vincristine.

It is further noted in the formula above that additive or substituent compounds such as amides and alkoxy compounds at $C_3$ and $C_4$ have been prepared from plant recovered vinblastine and vincristine.

In a broad sense the present method is applicable to the production of dimer products from catharanthine and dihydrocatharanthine with vindoline as starting materials and phenyl, alkyl and amide derivatives embraced by the following formulas:

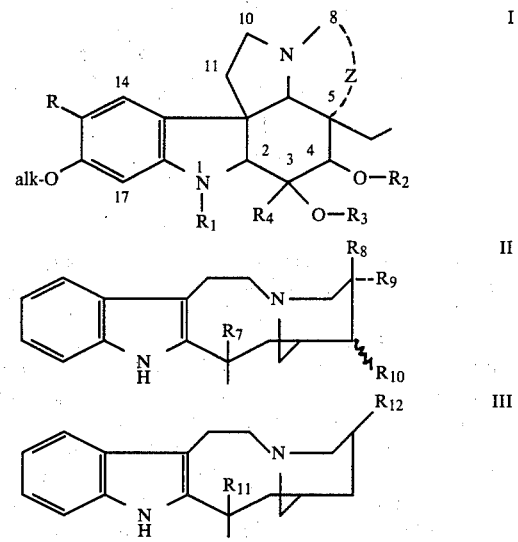

Formula I is as pictured and in that formula alk represents a lower alkyl group of $C_1$–$C_6$ and preferably $C_1$–$C_3$; aryl is mono-aryl such as benzyl, styryl, and xylyl; $R_1$ is a member of the group consisting of hydrogen, alk, CHO and $COR_5$ where $R_5$ is alkyl or aryl; $R_2$ and $R_3$ are members of the group consisting of hydrogen and —CO—alk; $R_4$ is a member of the group consisting of COO-alk, CONH—NH$_2$, CONH$_2$, CONHR$_6$, and CON(R$_6$)$_2$ where $R_6$ is alkyl; Z is a member of the group consisting of —CH$_2$—CH$_2$— and —CH=CH— and R is a member of the indole family represented by Formula II where $R_7$ is a member of the group consisting of hydrogen, or COO-alk; $R_8$ is a member of the group consisting of hydrogen, OH, O-alk, OCO-alk or alkyl; $R_9$ is a member of the group consisting of hydrogen, OH, O-alk, OCO-alk, or alkyl; $R_{10}$ is a member of the group consisting of hydrogen, OH, O-alk, OCO-alk, or Formula III where $R_{11}$ is a member of the group consisting of hydrogen or COO-alk; $R_{12}$ is a member consisting of alkyl.

Compounds represented by Formula I are prepared by contacting vindoline or a vindoline derivative, when R is hydrogen with an indole derivative represented by a compound of Formula IV where $R_{13}$ is a member of the group consisting of hydrogen or COO-alk or by a compound of Formula V where $R_{14}$ is a member of the group consisting of hydrogen or COO-alk and $R_{15}$ is a member of the group consisting of alkyl.

In Formulas I–VI and generally in this application and claims, alk and alkyl mean lower alkyl as defined in Formula I above and aryl means mono-aryl as similarly defined in Formula I.

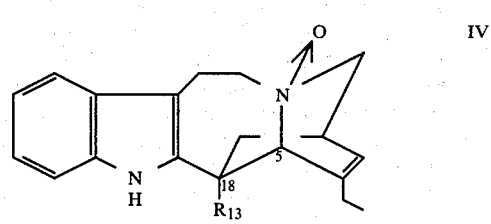

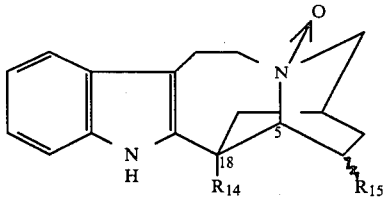

V

The so-called intermediates IV and V are not isolated during the process of the present invention and this factor is believed to significantly and favorably influence the stereochemistry to produce the natural isomers at $C_{18'}$. The conditions for the complete reaction including the formation of the NO compound IV and V as well as the formation of the indoledihydroindole dimers represented by Formula I are carried out in an inert organic solvent such as preferably methylene chloride containing trifluoroacetic anhydride. As alternatives for methylene chloride useful in producing the NO compound, there may be used other polyhalo organic solvents such as carbon tetrachloride, methylene bromide, and chloroform.

As alternative reagents for the trifluoroacetic anhydride component used in fragmentation and coupling, there may be utilized trichloroacetic anhydride, acetic anhydride, acetyl chloride, and tosyl anhydride. These reagents bring about a Polonovski-type fragmentation of the $C_5$–$C_{18}$ bond in the substances shown in Formulas IV and V.

The reaction temperature, time, and pressure conditions in general are similar to those employed in the Polonovski reaction which, in its original application, involved the dealkylation of tertiary and heterocyclic amines by acylation of the corresponding N-oxides with acetic anhydride or acetyl chloride (cf. Merck Index, 8th ed., 1968, page 1203). The temperature of the fragmentation reaction may vary from $-15°$ C. to $40°$ C. and preferably from $-10°$ C. to $+10°$ C. The portions of the reaction relating to the formation of the NO compound are conducted in the open but the coupling following the fragmentation portion of the reaction is conducted under cover with inert conditions such as nitrogen or an inert gas of Group Zero of the Periodic Table such as argon, neon, helium, etc., and under a positive temperature control of about $10°$ C. to $-10°$ C. In the present combined reaction where fragmentation and coupling occur sequentially, the temperature control preferred of $10°$ to $-10°$ C. and optimally $-10°$ C. for both fragmentation and coupling, together with an inert blanket is greatly preferred.

Due to the low temperature necessary for the latter stage reaction, the reaction time may vary from several hours to several days.

PRIOR ART

U.S. Pat. No. 3,422,112 Gorman et al—Similar dimeric alkaloidlike substances may be produced by reacting indoles with vindoline and the coupling reaction depends upon the reactivity of the 15 position in the vindoline molecule, which is ortho to an alkoxy group. The condensation or coupling reaction is achieved under mild conditions with a Friedel-Crafts type catalyst, such as aluminum or zinc chloride in benzene. No mention is made of achieving the natural desired stereo isomers.

The present reaction differs from the above prior art in both stages, which stages are conducted in a sequential manner without isolation of an intermediate. The preparation of the intermediate NO compounds represented by Formulas IV and V is achieved at various temperatures; for example, $-77°$ C., $0°$, room temperature and above, in an inert organic solvent such as methylene chloride described above and with a peracid such as m-chloroperbenzoic acid or p-nitroperbenzoic acid. The fragmentation reaction which fragments the $C_5$–$C_{18}$ bond in the catharanthine unit is carried out in the presence of a reagent such as trifluoroacetic anhydride. the subsequent coupling reaction promotes the formation of a natural dimer bonded at $C_{18'}$ (Catharanthine) and $C_{15}$ (vindoline) under an inert gas blanket preferably at a low temperature parameter control of $-10°$ C. to $+10°$ C.

As a final step in the present process, a reducing agent such as preferred alkali metal borohydride ($NaBH_4$, $KBH_4$, $LiBH_4$) is utilized which reduces the double bond on the immonium nitrogen of the catharanthine unit.

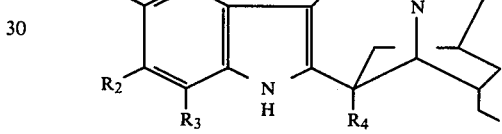

VI

In addition to catharanthine, any indole unit represented by Formula VI may be employed. In the above Formula VI, R, $R_1$, $R_2$ and $R_3$ are members of the group consisting of hydrogen, OH, O-alk, OCOalk, alkyl or aryl. In the above Formula VI, as previously stated, alk is lower alkyl $C_1$–$C_6$ and preferably $C_1$–$C_3$, and aryl is mono-aryl such as benzyl, xylyl, etc. The products of the present coupling reaction may be isolated from the reaction mixtures with standard procedures. Additionally, in some cases, due to the high complexity of the products, isolation by techniques as column, thin layer or high pressure liquid chromatography may be used.

THE STEREOCHEMISTRY OF THE DIMERS

The process of the present invention, as particularly applied to the reaction of catharanthine and vindoline, is technologically interesting, since the results show a successful adaptation to the product of the correct stereochemistry after coupling of $C_{18'}$ on the catharanthine fraction. Thus, it is conjectured that the present process may follow that of plant enzymes involved in biosynthesis of vinblastine and vincristine.

The schemat below involves a conversion of initial electrophilic attack at the β-position of the indole ring and subsequent fragmentation between positions 5 and 18 (see Scheme 1). On the other hand, conversion of catharanthine to its N-oxide allows a Polonovski-type fragmentation and an intermediate is formed which, if not separated, prefers dimers with natural stereochemistry at $C_{18'}$ as noted in XII below (see Scheme 2).

Scheme 1

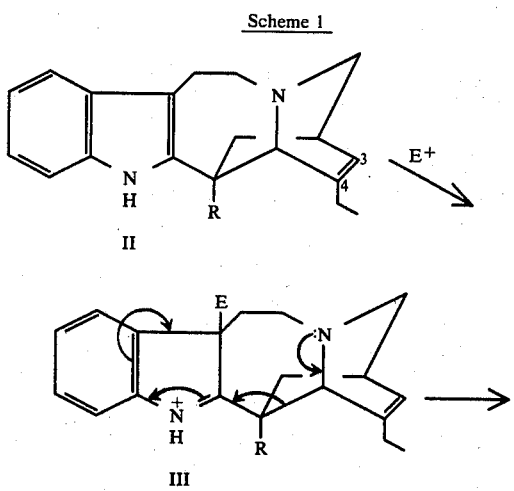

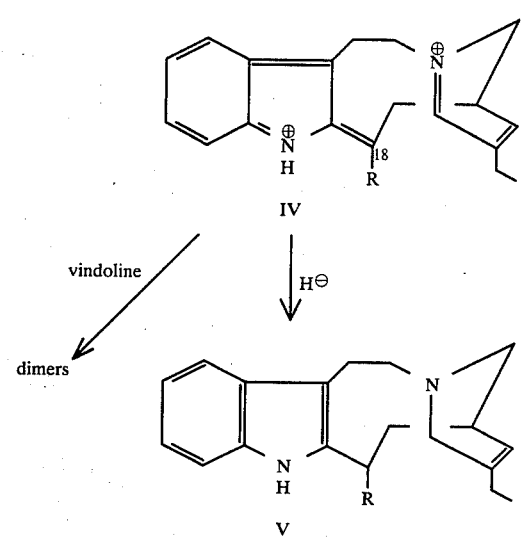

As shown in Scheme 2, if a concerted process is used wherein the intermediate is not isolated, the dimer forms in trans coplanar fashion and the resulting dimers possess natural stereochemistry at $C_{18'}$.

Tables 1 and 2 show the summary of results illustrating the preference of the preferential isolation and recovery of the preferred natural isomers XII and XV.

Scheme 2

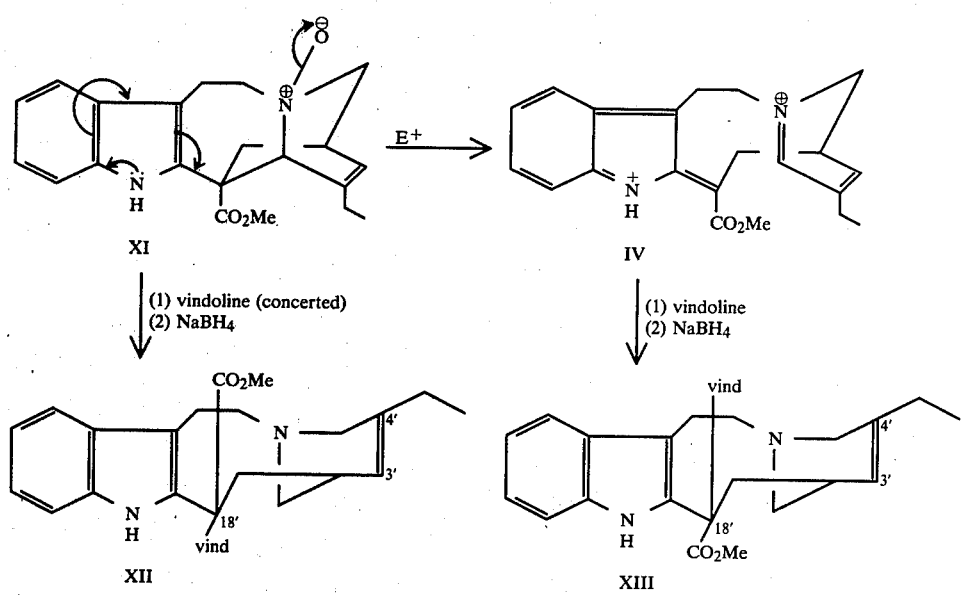

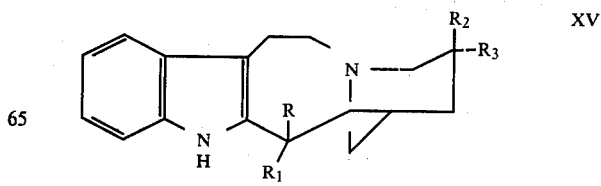

TABLE 1
Coupling of Vindoline with Various N-oxides

| Expt. | N-oxide Employed[a] | Coupling Conditions[e] | Dimers Isolated | (Yields)[f] |
|---|---|---|---|---|
| 1 | catharanthine[b] | HCl, CH$_3$OH, r.t. | XIV[g] | (30) |
| 2 | catharanthine[c] | (CF$_3$CO)$_2$O, −10° C. | XII | (30) |
|   |   |   | XIII | (14) |
| 3 | catharanthine[d] | (CF$_3$CO)$_2$O, −10° C. | XII | (14) |
|   |   |   | XIII | (31) |
| 4 | dihydrocatharanthine[c] (11, no 3,4-double bond) | (CF$_3$CO)$_2$O, −10° C. | XV, R = CO$_2$Me; R$_1$ = vind R$_2$ = CH$_2$CH$_3$; R$_3$ = H | (5) |
|   |   |   | XV, R = CO$_2$Me; R$_1$ = vind R$_2$ = H; R$_3$ = CH$_2$CH$_3$ | (13) |
|   |   |   | XV, R = vind, R$_1$ = CO$_2$Me R$_2$ = CH$_2$CH$_3$; R$_3$ = H | (14)[h] |
|   |   |   | XV, R = vind; R$_1$ = CO$_2$Me, R$_2$ = CH$_2$CH$_3$; R$_3$ = H |   |

[a]In all cases, m-chloroperbenzoic acid was employed to prepare N-oxide.
[b]Reaction was performed at room temperature and oxide purified by chromatography. During purification, N-oxide undergoes conversion to a new product, the structure of which remains undetermined at present.
[c]N-oxide prepared in situ.
[d]N-oxide isolated at low temperature.
[e]After coupling in each case the reaction mixture was treated with sodium borohydride prior to isolation of dimers.
[f]Yields quoted are not optimum. For example in related studies yields as high as 55% of XII have been obtained.
[g]Structure assignment based on spectral data only.
[h]Yield quoted on mixture of these dimers with unnatural stereochemistry at C$_{18'}$.

TABLE 2
Characterization Data for Isolated Dimers

| Dimer[a] | NMR[b,c] | MS[d] | | CD[e] | MP |
|---|---|---|---|---|---|
|  |  | C$_{46}$H$_{56}$O$_8$N$_4$ | | | |
|  |  | Requires | Obtained | | |
| XIV | 3.94 (s, C$_{17}$H) 2.30–3.00 (m, C$_{14}$H + aromatic) 5.72 (m, C$_{18'}$H) | 792.410 | 792.412 |  | amorphous |
| XII | 3.89 (s, C$_{17}$H) 3.54 (s, C$_{14}$H) | 792.410 | 792.405 | 227 nm(+27) | 171–173 (dec.) |
| XIII | 3.98 (s, C$_{17}$H) 3.05 (s, C$_{14}$H) | 792.410 | 792.399 | 224 nm(−31) | amorphous |
|  |  | C$_{46}$H$_{58}$O$_8$N$_4$ | | | |
|  |  | Requires | Obtained | | |
| XV R = CO$_2$Me; R$_1$ = vind; R = CH$_2$CH$_3$; R$_3$ = H | 3.87 (s, C$_{17}$H) 3.39 (s, C$_{14}$H) | 794.425 | 794.421 | 226 nm(+17) | amorphous |
| XV R = CO$_2$Me; R$_1$ = vind; R$_2$ = H; R$_3$ =CH$_2$CH$_3$ | 3.80 (s, C$_{17}$H) 3.42 (s, C$_{14}$H) | 794.425 | 794.422 | 227 nm(+26) | 190–194 (dec.) |
| XV[f] R = vind; R$_1$ = CO$_2$Me R$_2$ = CH$_2$CH$_3$; R$_3$ = H | 4.04 (s, C$_{17}$H) 3.05 (s, C$_{14}$H) | 794.425 | 794.419 | 223 nm(−29) | amorphous |

[a]UV spectra
[b]NMR spectra taken at 100 MHz and data is given in τ values.
[c]Aromatic proton signals given for the vindoline unit.
[d]Mass spectrometer data obtained on AEI MS902.
[e]CD study used to predict chirality at C$_{18'}$ in these dimers; results presented were obtained in methanol solution.
[f]Results corroborated with an analogous method proceeding from chloroindolenine.

Relative to Experiment 4, Table 1, and dimer XV products, it is noted that two of these possess the natural stereochemistry at C$_{18'}$. It is noted that the chirality at C$_4$, the ethyl bearing center, is apparent in this synthesis of bis indole alkaloids in the vinblastine vincristine series; the other two are in isomeric series obtained and characterized previously.

EXAMPLE 1

Preparation of 3'4'-Dehydrovinblastine

In Formula I,
Z = —CH=CH—
R$_1$ = CH$_3$
R$_2$ = COCH$_3$
R$_3$ = H
R$_4$ = COOCH$_3$
R = III
where
R$_{11}$ = COOCH$_3$
R$_{12}$ = CH$_2$CH$_3$ The reaction was performed under anhydrous conditions. All glassware was oven-dried at 120° C. The solvent, methylene chloride, and coupling reagent, trifluoroacetic anhydride were distilled from P$_2$O$_5$ prior to use.

To a solution of catharanthine (201 mg, 0.60 mmol) in methylene chloride (40 ml) at −15° C. was added a solution of m-chloroperbenzoic acid (111 mg, 0.65 mmol) and the solution stirred for 15 min. To the catharanthine N-oxide thus formed was added a solution of vindoline (270 mg, 0.59 mmol) in methylene chloride. The atmosphere in the reaction flask was then replaced with nitrogen and the remainder of the coupling carried out in this inert atmosphere. Trifluoroacetic anhydride (0.41 ml, 3.01 mmol) was added to the stirred solution maintained at $-15°$ C. After 22 hours this mixture was added to a solution of sodium borohydride in ethanol. After the initial vigorous evolution of gas, water and additional methylene chloride was added to the reaction mixture. The organic phase was separated and the aqueous layer washed with a second portion of methylene chloride. The organic portions were combined and washed with a solution of $K_2CO_3$. The organic phase was separated and dried with $Na_2SO_4$. The solvent was evaporated in vacuo and the residue dissolved in hot acetone. The solution was cooled and crystals of 3'4'-dehydrovinblastine were isolated. The mother liquors from the crystallization were chromatographed on silica gel plates using methanol-ethyl acetate as the eluting solvent. The combined fractions of 3'4'-dehydrovinblastine, mp 171°–173° obtained from these purifications amounted to 226 mg (0.29 mmol). Calc. for $C_{46}H_{56}O_8N_4$: 792.410. Found: 792.405.

Analysis of this product proved that it had the correct isomerism to coincide with the natural isomer.

A small amount (36.8 mg, 0.05 mmol) of the $C_{18'}$-epimer of 3'4'-dehydrovinblastine was also obtained from this reaction.

The portion of the process relating to coupling was carried out under inert conditions; i.e., with nitrogen or an inert gas of the argon family.

EXAMPLE 2

Preparation of 4'-Deoxovinblastine

In Formula I,
Z=—CH=CH—
$R_1$=CH$_3$
$R_2$=COCH$_3$
$R_3$=H
$R_4$=COOCH$_3$
R=II
where
$R_7$=COOCH$_3$
$R_8$=H
$R_9$=CH$_2$CH$_3$
$R_{10}$=H
and 4'-Deoxo-4'-Epivinblastine In Formula I,
Z=—CH=CH—
$R_1$=CH$_3$
$R_2$=COCH$_3$
$R_3$=H
$R_4$=COOCH$_3$
R=II
where
$R_7$=COOCH$_3$
$R_8$=CH$_2$CH$_3$
$R_9$=H
$R_{10}$=H Dihydrocatharanthine (0.0506 gms., 0.00015 M) was dissolved in dry methylene chloride (10 ml) and the solution cooled to $-15°$ C. with care to exclude moisture. M-Chloroperbenzoic acid (0.0293 gm, 0.00017 M) dissolved in dry methylene chloride (1 ml), was added dropwise over a period of fifteen minutes after which time the reaction mixture was checked by TLC which indicated no dihydrocatharanthine remained. Vindoline (0.0721 gms, 0.00016 M) was added directly to the reaction mixture followed by trifluoroacetic anhydride (0.1 ml, 0.0007 M) and the reaction allowed to stand at $-15°$ C. for eighteen hours under a nitrogen atmosphere. The reaction mixture was then added to a solution of sodium borohydride (1 gm) in methanol (10 ml) and the whole stirred for fifteen minutes at 0° C. The organic solvents were removed in vacuo, the residue dissolved in water (25 ml) and the resulting solution extracted with ethyl acetate (3×10 ml). The combined organic phase was dried over sodium sulphate. The product obtained after removal of organic solvent was subjected to preparative TLC on silica eluting with ethyl acetate: methanol (65:35). Three bands were removed $R_f$=0.013, 0.042, 0.031 which contained 4'-deoxovinblastine (15.7 mgms, 0.00002 M), 4'-deoxo-4'-epi vinblastine (5.7 mgms, 0.000007 M) and a mixture (13.5 mgms, 0.000017 M) of their $C_{18'}$ epimers respectively.

4'-deoxovinblastine: Calc. for $C_{46}H_{58}O_8N_4$: 794.425. Found: 794.421.

4'-deoxo-4'-epivinblastine: Calc. for $C_{46}H_{58}O_8N_4$: 794.425. Found: 794.422.

I claim:

1. A process for the production of compounds represented by the following formulas

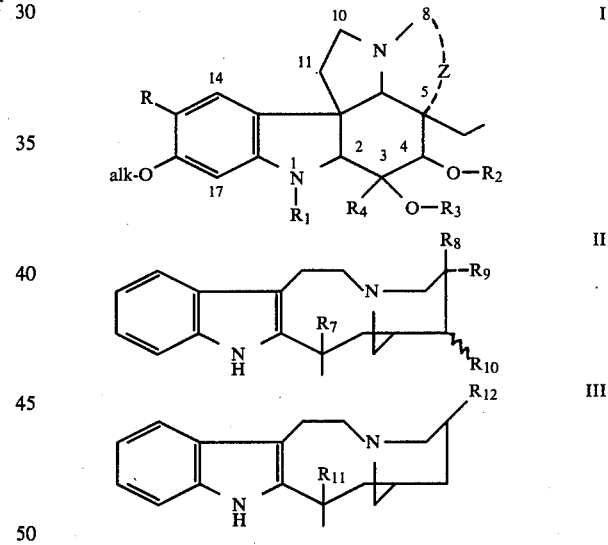

wherein in Formula I
Alkyl=CH$_3$
$R_1$=CH$_3$
$R_2$=COCH$_3$
$R_3$=H
$R_4$=COOCH$_3$
Z=—CH=CH—
R=II or III
$R_7$=COOCH$_3$
$R_8$=H or C$_2$H$_5$
$R_9$=H or C$_2$H$_5$
$R^{10}$=H
$R^{11}$=COOCH$_3$
$R^{12}$=C$_2$H$_5$
wherein the process is for the synthesis of a dimer derived from an indole unit of the natural Iboga alkaloid family containing an aza bicyclo-octane portion and a dihydroindole unit of the natural Aspidosperma and Vinca alkaloid family, the stereochemistry of the carbon-carbon linkage between these units being identical with that of vinblastine which consists of (a) forming an N-oxide intermediate in the cold at a temperature of −10° to +10° C. from said indole unit by oxidizing the bridge nitrogen and without isolating said intermediate;

(b) treating said N-oxide indole intermediate in the presence of one member of the group consisting of acetic anhydride, halogenated acetic anhydride, and acetyl chloride to effect a Polonovski-type fragmentation reaction;

(c) without isolating the product of step (b), coupling said reaction product with a dihydroindole unit in the presence of acetic anhydride, halogenated acetic anhydride, and acetyl chloride at a low temperature of about −10° C. to +10° C. under inert conditions; and (d) subsequently, without isolating said coupled product, reducing the immonium nitrogen on the indole unit by reacting with aqueous alkali metal borohydride to produce the dimer, in which the improvement comprises in step (a) the non-isolation of said intermediate.

2. The process according to claim 1 wherein the indole unit is catharanthine and the dihydroindole unit is vindoline, which are coupled to produce a dimer having the same stereochemistry as vinblastine and bonded at aliphatic $C_{18'}$ in catharanthine and at aromatic $C_{15}$ in vindoline.

3. The process of claim 1 wherein the preferred solvent for producing the NO compound is methylene chloride.

4. The process of claim 1 wherein the preferred solvent for the coupling reaction is trifluoroacetic anhydride.

5. The process of claim 1 wherein during the coupling segment of the process the reaction temperature is maintained at about −10° C.

* * * * *